US011566927B2

(12) United States Patent
Tateishi et al.

(10) Patent No.: US 11,566,927 B2
(45) Date of Patent: Jan. 31, 2023

(54) OPTICAL MEASUREMENT APPARATUS, OPTICAL MEASUREMENT METHOD, COMPUTER PROGRAM, AND RECORDING MEDIUM

(71) Applicants: PIONEER CORPORATION, Tokyo (JP); NIKKISO COMPANY LIMITED, Tokyo (JP)

(72) Inventors: Kiyoshi Tateishi, Kawagoe (JP); Mitsuru Sato, Kawagoe (JP); Tadashi Kondo, Kawagoe (JP); Wataru Onodera, Kawagoe (JP); Tomoya Murakami, Makinohara (JP); Akari Agata, Makinohara (JP); Genki Adachi, Makinohara (JP)

(73) Assignees: AIR WATER BIODESIGN INC., Hyogo (JP); NIKKISO COMPANY LIMITED, Tokyo (JP)

( * ) Notice: Subject to any disclaimer, the term of this patent is extended or adjusted under 35 U.S.C. 154(b) by 0 days.

(21) Appl. No.: 16/648,993

(22) PCT Filed: Sep. 21, 2017

(86) PCT No.: PCT/JP2017/034095
§ 371 (c)(1),
(2) Date: Mar. 19, 2020

(87) PCT Pub. No.: WO2019/058482
PCT Pub. Date: Mar. 28, 2019

(65) Prior Publication Data
US 2020/0284628 A1 Sep. 10, 2020

(51) Int. Cl.
G01F 1/661 (2022.01)
A61B 5/026 (2006.01)
(Continued)

(52) U.S. Cl.
CPC .......... *G01F 1/661* (2013.01); *A61B 5/0261* (2013.01); *A61B 5/0285* (2013.01); *A61M 1/3663* (2013.01); *G01P 5/26* (2013.01)

(58) Field of Classification Search
CPC ........ G01S 7/4812; G01S 17/58; G01S 7/497; G01S 7/493; G01S 7/4916; G01S 2007/4977; G01P 5/26; G01F 1/661
See application file for complete search history.

(56) References Cited

U.S. PATENT DOCUMENTS

2005/0047454 A1 3/2005 Williamson
2006/0072638 A1 4/2006 Tanaka
(Continued)

FOREIGN PATENT DOCUMENTS

EP 2837327 A1 2/2015
JP S63-61380 A 3/1988
(Continued)

OTHER PUBLICATIONS

Translation for WO2016046905 2016 (Year: 2016).*
(Continued)

*Primary Examiner* — Luke D Ratcliffe
(74) *Attorney, Agent, or Firm* — Nixon & Vanderhye

(57) ABSTRACT

An optical measurement device is provided with: a light source that irradiates, with light, a measurement object which has a fluid flowing thereinside; a light receiving unit which, upon receipt of scattered light from the measurement object irradiated with light, outputs a light reception signal according to the intensity of the scattered light; a disturbance generation unit which generates a disturbance signal for causing oscillation of a drive current to be supplied to the light source; and an adjustment unit which adjust the drive
(Continued)

current on the basis of the result of a comparison between the disturbance signal and a signal generated on the basis of the light reception signal.

14 Claims, 7 Drawing Sheets

(51) Int. Cl.
  *A61B 5/0285* (2006.01)
  *A61M 1/36* (2006.01)
  *G01P 5/26* (2006.01)

(56) References Cited

U.S. PATENT DOCUMENTS

| | | | | |
|---|---|---|---|---|
| 2007/0002013 A1* | 1/2007 | Kong | ................... | G06F 3/0312 345/157 |
| 2009/0174931 A1* | 7/2009 | Huber | ................... | H01S 3/1106 372/18 |

FOREIGN PATENT DOCUMENTS

| | | |
|---|---|---|
| JP | H08-18145 A | 1/1996 |
| JP | 2001-120509 A | 5/2001 |
| JP | 5806390 B2 | 11/2015 |
| WO | 2015/198472 A1 | 12/2015 |
| WO | 2016/046905 A1 | 3/2016 |
| WO | WO2016046905 * 3/2016 ............. G01B 11/00 |

OTHER PUBLICATIONS

International Search Report, dated Oct. 17, 2017, from corresponding PCT application No. PCT/JP2017/034095.
Extended European Search Report issued in European Patent Application No. 17 925 672.2 dated Apr. 27, 2021.
Heumier, T.A. et al., "Mode Hopping in Semiconductor Lasers," 2005, XP055443285, Retrieved from the Internet: URL:https://www.newport.com/medias/sys master/images/images/h4b/h48/8797049585694/AN08-Mode-Hopping-in-Semiconductor-Laser-Diodes.pdf [retrieved on Jan 23, 2018].
Olsen, W. et al.,"A Standard for Measuring Transient Suppression of Laser Diode Drivers," Technical Standard #LDC-00196, 2003, pp. 1-10, XP055787867, Retrieved from the Internet: URL:https://www.newport.com/medias/sys master/images/images/hdf/h28/8797304717342/WP-A-Standard-for-Measuring-Transient-Suppression-of-Laser-Diode-Drivers.pdf [retrieved on Mar. 19, 2021].

* cited by examiner

US 11,566,927 B2

OPTICAL MEASUREMENT APPARATUS, OPTICAL MEASUREMENT METHOD, COMPUTER PROGRAM, AND RECORDING MEDIUM

TECHNICAL FIELD

The present invention relates to an optical measurement apparatus for and an optical measurement method of measuring, for example, a state of a measurement target by using light, a computer program, and a recording medium.

BACKGROUND ART

This type of apparatus is designed, for example, to prevent a change in properties of light emitted from a light source. For example, Patent Literature 1 discloses a technology/technique of stabilizing an oscillation wavelength of a laser diode (LD) by detecting the oscillation wavelength of the LD with an etalon, which is a wavelength discrimination device, and by controlling a LD drive current and a LD temperature. Alternatively, Patent Literature 2 discloses a technology/technique of stabilizing the oscillation wavelength of the LD by detecting the oscillation wavelength of the LD with a spectroscope that uses absorption spectra of molecules or atoms, and by controlling the LD drive current and the LD temperature. Moreover, Patent Literature 3 discloses a technology/technique of removing a random mode hop of the oscillation wavelength by superimposing an alternating current on a direct current supplied to the laser diode.

CITATION LIST

Patent Literature

Patent Literature 1: Japanese Patent Application Laid Open No. H08-018145
Patent Literature 2: Japanese Patent Application Laid Open No. S63-064380
Patent Literature 3: Japanese Patent Application Laid Open No. 2001-120509

SUMMARY OF INVENTION

Technical Problem

In the technologies/techniques described in the Patent Literatures 1 and 2, a complicated optical system may increase a size of an apparatus, or the use of a relatively expensive member, such as, for example, the spectroscope that uses absorption spectra of molecules or atoms, may increase a manufacturing cost. In the technology/technique described in the Patent Literature 3, the mode hope can be removed, but there is still room for improvement.

In view of the aforementioned problems, it is therefore an object of the present invention to provide an optical measurement apparatus and an optical measurement method that can relatively simply prevent a change in the properties of light emitted from a light source, a computer program, and a recording medium.

Solution to Problem

The above object of the present invention can be achieved by an optical measurement apparatus provided with: a light source configured to irradiate a measurement target in which fluid flows, with light; a light receiver configured to receive scattered light of irradiated light from the measurement target and configured to output a light receiving signal corresponding to intensity of the scattered light; a disturbance generator configured to generate a disturbance signal for fluctuating a drive current, which is supplied to the light source; and an adjuster configured to adjust the drive current on the basis of a result of a comparison between a signal generated on the basis of the light receiving signal and the disturbance signal.

The above object of the present invention can be also achieved by an optical measurement method in an optical measurement apparatus including: a light source configured to irradiate a measurement target in which fluid flows, with light; and a light receiver configured to receive scattered light of irradiated light from the measurement target and configured to output a light receiving signal corresponding to intensity of the scattered light, the optical measurement method provided with: a process of generating a disturbance signal for fluctuating a drive current, which is supplied to the light source; and a process of adjusting the drive current on the basis of a result of a comparison between a signal generated on the basis of the light receiving signal and the disturbance signal.

The above object of the present invention can be also achieved by a computer program for making a computer, which is provided in an optical measurement apparatus including: a light source configured to irradiate a measurement target in which fluid flows, with light; and a light receiver configured to receive scattered light of irradiated light from the measurement target and configured to output a light receiving signal corresponding to intensity of the scattered light, function as: a disturbance generator configured to generate a disturbance signal for fluctuating a drive current, which is supplied to the light source; and an adjuster configured to adjust the drive current on the basis of a result of a comparison between a signal generated on the basis of the light receiving signal and the disturbance signal.

The above object of the present invention can be also achieved by a recording medium on which the computer program of the present invention is recorded.

The effect of the present invention and other benefits will become apparent from the following description of embodiments.

DESCRIPTION OF EMBODIMENTS

Figure 1:
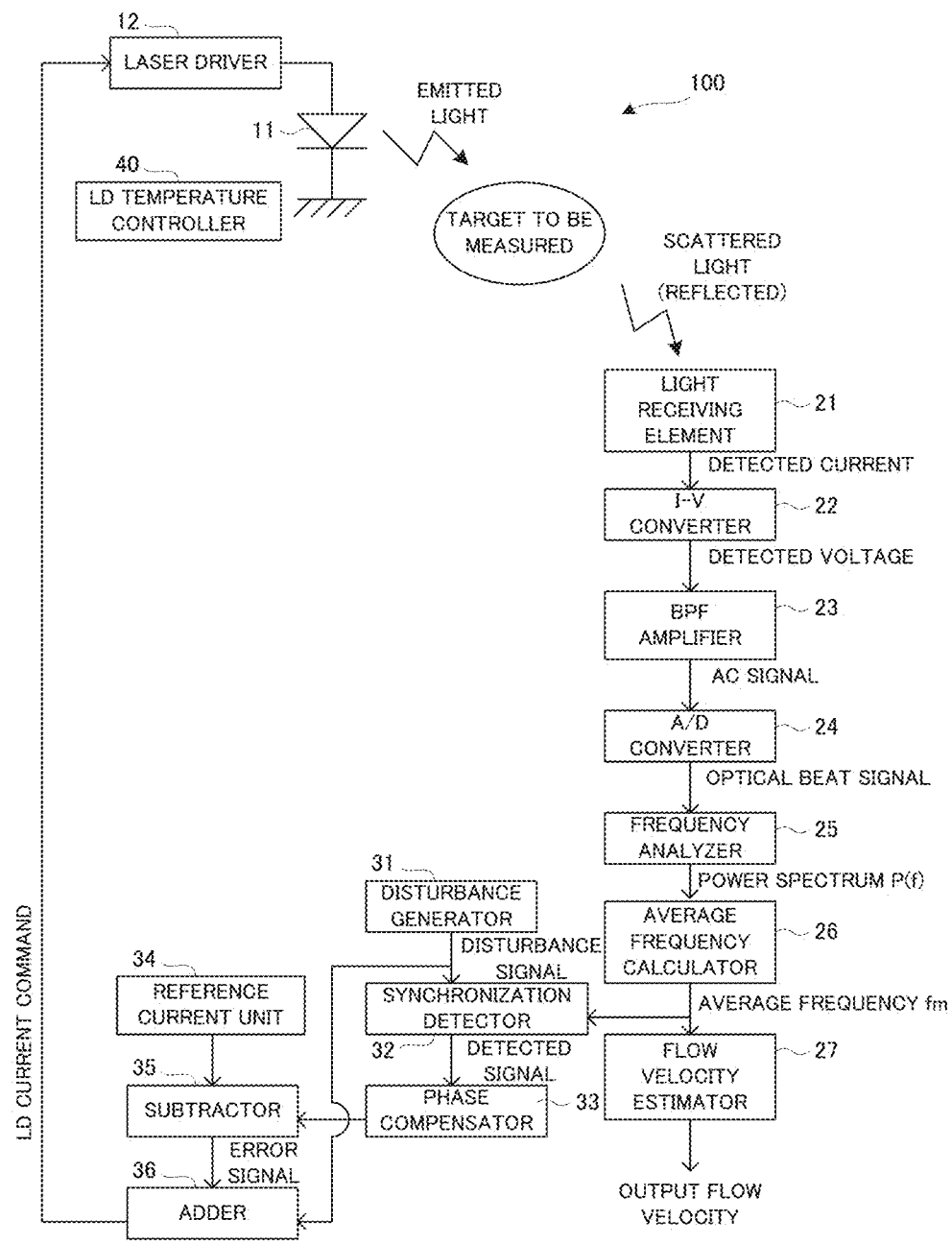
FIG. 1 is a block diagram illustrating a configuration of an optical measurement apparatus according to a first practical example.

An optical measurement apparatus, an optical measurement method, a computer program, and a recording medium according to embodiments of the present invention will be explained.

(Optical Measurement Apparatus)

An optical measurement apparatus according to an embodiment is provided with: a light source configured to irradiate a measurement target in which fluid flows, with light; a light receiver configured to receive scattered light of irradiated light from the measurement target and configured to output a light receiving signal corresponding to intensity of the scattered light; a disturbance generator configured to generate a disturbance signal for fluctuating a drive current, which is supplied to the light source; and an adjuster configured to adjust the drive current on the basis of a result of a comparison between a signal generated on the basis of the light receiving signal and the disturbance signal.

If the drive current is fluctuated by the disturbance signal, the intensity of the light emitted from the light source also fluctuates. As a result, the signal generated on the basis of the light receiving signal also fluctuates. Here, the studies by the present inventors have revealed that if interference of light, which is a property of the light emitted from the light source, changes due to a change in environmental temperature, the result of the comparison between the signal generated on the basis of the light receiving signal and the disturbance signal also changes. Thus, if the drive current is adjusted on the basis of the result of the comparison, it is possible to prevent a change in the interference of the light emitted from the light source. As described above, according to the optical measurement apparatus, it is possible to relatively simply prevent a change in the properties of light.

In an aspect of the optical measurement apparatus according to the embodiment, the signal generated on the basis of the light receiving signal is a signal indicating frequency information, which is obtained by performing a frequency analysis on a beat signal, which is included in the light receiving signal and which is caused by a Doppler shift of the irradiation light. According to this aspect, it is possible to relatively easily compare the signal generated on the basis of the light receiving signal with the disturbance signal.

In this aspect, the signal indicating the frequency information may be compared with the disturbance signal after being passed through a filter for selectively passing a frequency component of a predetermined frequency band, which includes a frequency associated with the disturbance signal. By virtue of such a configuration, it is possible to prevent an influence of noise.

In another aspect of the optical measurement apparatus according to the embodiment, the fluid is transferred by a pump, and a frequency associated with the disturbance signal is higher than a pulsation frequency of the fluid, which is caused by the pump. According to this aspect, it is possible to prevent that the result of the comparison between the signal generated on the basis of the light receiving signal and the disturbance signal is influenced by the pump.

In another aspect of the optical measurement apparatus according to the embodiment, the light source is a semiconductor laser, and the adjuster is configured to adjust the drive current on the basis of the result of the comparison such that the semiconductor laser oscillates in a single mode. According to this aspect, it is possible to keep a light power of the semiconductor laser relatively low, and it is also possible to set a signal to noise (SN) ratio of the light receiving signal to be relatively high.

In another aspect of the optical measurement apparatus according to the embodiment, it is provided with: a temperature controller configured to control a temperature of the light source; and a temperature setting device (i) configured to obtain a relation between the temperature of the light source and interference of the light emitted from the light source, while controlling the temperature controller to change the temperature of the light source, and (ii) configured to set a target temperature associated with the temperature controller on the basis of the obtained relation, before measurement of the measurement target. According to this aspect, it is possible to relatively easily set the target temperature.

In another aspect of the optical measurement apparatus according to the embodiment, it is provided with: a first determinator configured to determine whether or not the fluid includes a scatterer on the basis of the light receiving signal; and a first light source controller configured to control a power of the light emitted from the light source, on the basis of a determination result of the first determinator. According to this aspect, it is possible to prevent that the drive current is inappropriately supplied to the light source, due to the fluid that does not include the scatterer.

In another aspect of the optical measurement apparatus according to the embodiment, it is provided with: a light amount monitor configured to detect a power of the light emitted from the light source; a second determinator configured to determine whether or not the detected power is within a predetermined range; and a second light source controller configured to control the power of the light emitted from the light source, on the basis of a determination result of the second determinator. According to this aspect, it is possible to prevent that the drive current is inappropriately supplied to the light source.

In another aspect of the optical measurement apparatus according to the embodiment, it is provided with: a gain selector configured to change an amplitude of the disturbance signal generated by the disturbance generator. According to this aspect, it is possible to set a time required for the adjustment of the drive current based on the result of the comparison between the signal generated on the light receiving signal and the disturbance signal, which is performed by the adjuster, to be relatively short.

(Optical Measurement Method)

An optical measurement method according to an embodiment is an optical measurement method in an optical measurement apparatus including: a light source configured to irradiate a measurement target in which fluid flows, with light; and a light receiver configured to receive scattered light of irradiated light from the measurement target and configured to output a light receiving signal corresponding to intensity of the scattered light, the optical measurement method provided with: a process of generating a disturbance signal for fluctuating a drive current, which is supplied to the light source; and a process of adjusting the drive current on the basis of a result of a comparison between a signal generated on the basis of the light receiving signal and the disturbance signal.

According to the optical measurement method in the embodiment, as in the optical measurement apparatus in the embodiment described above, it is possible to relatively simply prevent a change in the properties of light. Even the optical measurement method according to the embodiment can also adopt the same various aspects as those of the optical measurement apparatus according to the embodiment described above.

(Computer Program)

A computer program according to an embodiment makes a computer, which is provided in an optical measurement apparatus including: a light source configured to irradiate a measurement target in which fluid flows, with light; and a light receiver configured to receive scattered light of irradiated light from the measurement target and configured to output a light receiving signal corresponding to intensity of the scattered light, function as: a disturbance generator configured to generate a disturbance signal for fluctuating a drive current, which is supplied to the light source; and an adjuster configured to adjust the drive current on the basis of a result of a comparison between a signal generated on the basis of the light receiving signal and the disturbance signal.

According to the computer program in the embodiment, the optical measurement apparatus according to the embodiment described above can be relatively easily realized by making the computer, which is provided in the optical measurement apparatus, execute the computer program. As a result, according to the computer program in the embodiment, as in the optical measurement apparatus according to the embodiment described above, it is possible to relatively simply prevent a change in the properties of light.

(Recording Medium)

On a recording medium according to an embodiment, the computer program according to the embodiment described above is recorded. The optical measurement apparatus according to the embodiment described above can be relatively easily realized as the computer provided in the optical measurement apparatus reads and executes the computer program recorded on a compact disc read only memory (CD-ROM), a DVD read only memory (DVD-ROM), or the like, which is an example of the recording medium according to the embodiment. As a result, according to the recording medium in the embodiment, as in the optical measurement apparatus according to the embodiment described above, it is possible to relatively simply prevent a change in the properties of light.

Practical Examples

An optical measurement apparatus according to practical examples of the present invention will be explained with reference to the drawings. In the practical examples below, blood is exemplified as fluid. Moreover, a tubing that constitutes a blood circuit of an artificial dialysis apparatus is exemplified as a measurement target. The optical measurement apparatus according to the present invention can be also applied to the measurement of blood that flows in veins of a living body, or any fluid other than the blood (e.g., ink, oil, wastewater or sewage, a seasoning, etc.).

First Practical Example

An optical measurement apparatus according to a first practical example of the present invention will be explained with reference to FIG. 1 to FIG. 11(b).

(Configuration of Optical Measurement Apparatus)

A configuration of the optical measurement apparatus according to the first practical example will be explained with reference to FIG. 1. FIG. 1 is a block diagram illustrating the configuration of the optical measurement apparatus according to the first practical example.

In FIG. 1, an optical measurement apparatus 100 is provided with a semiconductor laser 11, a laser driver 12, a light receiving element 21, an I-V converter 22, a band-pass filter (BPF) amplifier 23, an analog to digital (A/D) converter 24, a frequency analyzer 25, an average frequency calculator 26, a flow velocity estimator 27, a disturbance generator 31, a synchronization detector 32, a phase compensator 33, a reference current unit 34, a subtractor 35, and an adder 36.

The laser driver 12 is configured to generate an electric current for driving the semiconductor laser 11 (specifically, a specified drive current that is greater than or equal to a threshold current of the semiconductor laser 11). The semiconductor laser 11 is configured to perform laser oscillation in accordance with the drive current generated by the laser driver 12. An extracorporeal circulation blood circuit, which is a target to be measured (i.e., a transparent tubing in which blood flows), is irradiated with laser light emitted from the semiconductor laser 11, via an optical system (not illustrated), such as, for example, a lens element. The irradiated laser light may be scattered and absorbed by the tubing that constitutes the extracorporeal circulation blood circuit and by the blood that flows in the tubing.

The extracorporeal circulation blood circuit is semi-fixed to a casing (not illustrated) in which the semiconductor laser 11 and the light receiving element 21 are mounted and fixed, so that an irradiation position is not shifted due to vibration or the like.

The light receiving element 21 is configured to receive scattered light (which is reflected light herein) of the laser light with which the target to be measured is irradiated.

The scattered light received by the light receiving element 21 may include scattered light scattered by the blood that flows in the tubing that constitutes the extracorporeal circulation blood circuit (particularly, by red blood cells, which is a moving scatterer included in the blood) and scattered light scattered by a structure that stands still, such as the tubing.

The light receiving element 21 is configured to output a detected current, which corresponds to intensity of the received scattered light. The I-V converter 22 is configured to convert the detected current outputted from the light receiving element 21, to a voltage signal (refer to "DETECTED VOLTAGE" in FIG. 1).

Here, the scattered light that enters the light receiving element 21 may include scattered light scattered by a structure that stands still (e.g., the tubing that constitutes the extracorporeal circulation blood circuit, etc.) and scattered light scattered by red blood cells included in the blood, which is a moving object. In the scattered light scattered by the red blood cells, the Doppler shift occurs in accordance with a moving velocity of the red blood cells.

Thus, the scattered light scattered by the structure that stands still and the scattered light scattered by the red blood cells interfere due to coherence of the laser light. The detected current outputted from the light receiving element 21 may include an optical beat signal that results from this interference.

Figure 2:
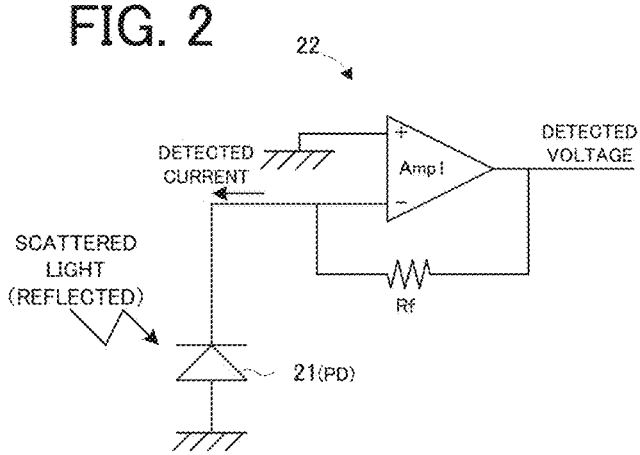
FIG. 2 is a circuit diagram illustrating an example of a light receiving element and an I-V converter according to the first practical example.

Now, an example of the light receiving element 21 and the I-V converter 22 will be explained with reference to FIG. 2. FIG. 2 is a circuit diagram illustrating an example of the light receiving element 21 and the I-V converter 22 according to the first practical example.

In FIG. 2, the light receiving element 21 is provided with a photodetectors PD, which is, for example, a PIN type semiconductor. The I-V converter 22 is provided with an amplifier Amp1 and a feedback resistor Rf. Here, the amplifier Amp1 constitutes a so-called transimpedance amplifier.

An anode of the photodetector PD is connected to a reference potential, such as, for example, a ground potential. A cathode of the photodetector PD is connected to an inverting input terminal of the amplifier Amp1. A non-inverting input terminal of the amplifier Amp1 is connected to the reference potential, such as, for example, a ground potential.

The detected current outputted from the photodetector PD is converted to voltage by the feedback resistor Rf, and is outputted from the amplifier Amp1 as the detected voltage (i.e., the voltage signal).

Back in FIG. 1 again, the BPF amplifier 23 is configured to cut a high frequency component and a low frequency component (i.e., signal components other than a predetermined frequency band), which are included in the voltage signal outputted from the I-V converter 22, and is configured to amplify the rest. The voltage signal outputted from the I-V converter 22 may include a high frequency signal, which is a noise component, such as, for example, a switching power supply noise. The voltage signal outputted from the I-V converter 22 is inputted to the BPF amplifier 23, by which it is possible to amplify the signal while reducing the noise component.

The A/D converter 24 is configured to perform an A/D conversion process (i.e., a quantization process) on an AC signal, which is a signal outputted from the BPF amplifier 23. As a result, an optical beat signal is outputted from the A/D converter 24.

The frequency analyzer 25 is configured to perform frequency analysis, such as fast Fourier transform (FFT), on the optical beat signal, for example, by digital signal processing (DSP) and to output a power spectrum P(f).

The average frequency calculator 26 is configured to calculate an average frequency fm on the basis of the power spectrum P(f).

Figure 3:
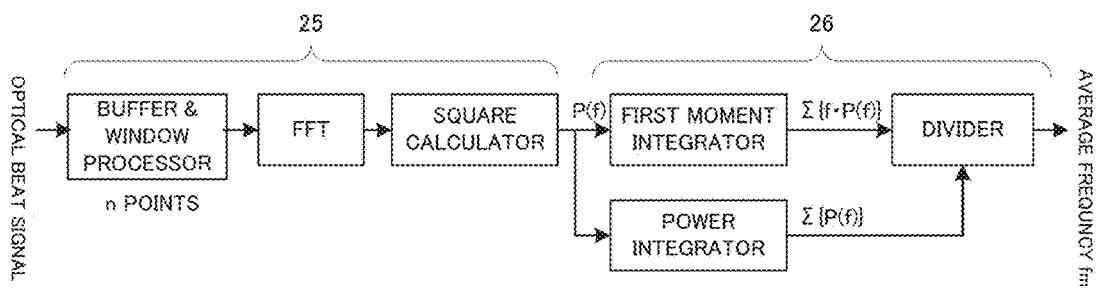
FIG. 3 is a conceptual diagram illustrating an example of a frequency analyzer and an average frequency calculator according to the first practical example.

Now, a specific example of each of the frequency analyzer 25 and the average frequency calculator 26 will be explained with reference to FIG. 3. FIG. 3 is a conceptual diagram illustrating an example of the frequency analyzer 25 and the average frequency calculator 26 according to the first practical example.

In FIG. 3, regarding the optical beat signal outputted from the A/D converter 24, accumulated data rows associated with the optical beat signal of n points are preprocessed to perform FFT, for example, by the Hanning window, on a buffer & window processor of the frequency analyzer 25. Then, on a FFT unit, FFT calculation of n points is performed on data limited by a window function of the Hanning window. A result of the FFT calculation by the FFT unit is subject to complex conjugate processing by a square calculator, and then, data of n/2 points is outputted as the power spectrum P(f).

A first moment integrator of the average frequency calculator 26 is configured to multiply the power spectrum P(f) and a frequency vector f and to integrate them in a specified band (which is f0 to f1 herein), thereby outputting $1\text{stM}=\Sigma\{f \cdot P(f)\}$ as a first moment. A power integrator of the average frequency calculator 26 is configured to integrate the power spectrum P(f) in a specified band (which is f0 to f1 herein), thereby outputting $Ps=\Sigma\{P(f)\}$. A divider of the average frequency calculator 26 is configured to divide the first moment 1stM by Ps, which is the output of the power integrator, and to output an obtained value as the average frequency fm.

Figure 4:
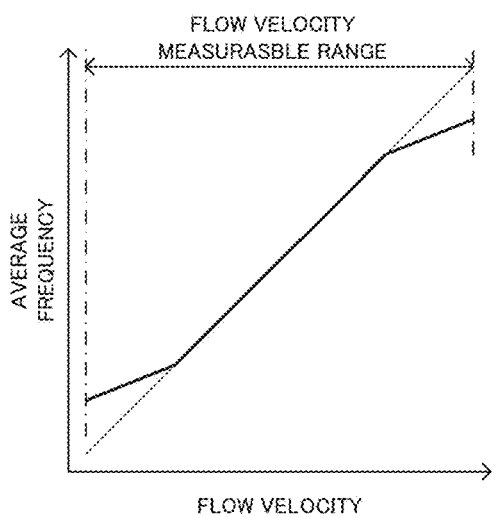
FIG. 4 is a diagram illustrating an example of a relation between a flow velocity and an average frequency.

A relation between a flow velocity of the blood that flows inside the target to be measured and the average frequency fm is, for example, as illustrated in FIG. 4. Specifically, the relation between the flow velocity and the average frequency fm may indicate that the flow velocity increases with increasing average frequency fm. As illustrated in FIG. 4, linearity decreases in an area in which the flow velocity is relatively high and in an area in which the flow velocity is relatively low. As a result, a measurable flow velocity range is naturally limited. In the area in which the flow velocity is relatively low, the linearity decreases due to a reduced SN ratio of the average frequency fm. On the other hand, in the area in which the flow velocity is relatively high, the linearity decreases due to restrictions by a sampling frequency of the A/D converter 24 and a bandwidth of the BPF amplifier 23.

Back in FIG. 1 again, the flow velocity estimator 27 is configured to estimate the flow velocity, from the average frequency fm outputted from the average frequency calculator 26, for example, by using a table associated with the relation between the flow velocity and the average frequency fm illustrated in FIG. 4. In other words, the optical measurement apparatus 100 constitutes an apparatus of estimating a flow velocity of scattered fluid by so-called laser flowmetry.

Figure 5:
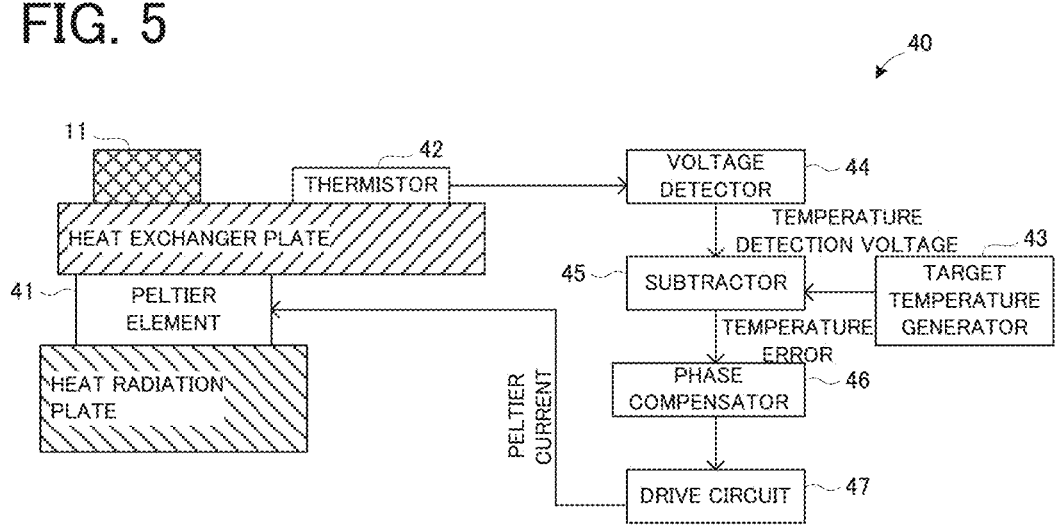
FIG. 5 is a block diagram illustrating a configuration of an LD temperature controller according to the first practical example.

The optical measurement apparatus 100 is further provided with a laser diode (LD) temperature controller 40. Now, the LD temperature controller 40 will be explained with reference to FIG. 5. FIG. 5 is a block diagram illustrating a configuration of the LD temperature controller according to the first practical example.

In FIG. 5, the LD temperature controller 40 is provided with a Peltier element 41, a thermistor 42, a target temperature generator 43, a voltage detector 44, a subtractor 45, a phase compensator 46, and a drive circuit 47. The semiconductor laser 11 is placed on one side of the Peltier element 41 via a heat exchanger plate. Heat generated in the semiconductor laser 11 is released to an external environment via the heat exchanger plate, the Peltier element 41, and a heat radiation plate.

The thermistor 42 is thermally coupled to the heat exchanger plate. The thermistor 42 constitutes a bridge circuit together with a reference resistor (not illustrated), and its middle point is connected to the voltage detector 44. The thermistor 42 may be an NTC thermistor. In the NTC thermistor, electric resistance thereof decreases with increasing temperature. Thus, a middle point voltage changes depending on temperature.

A thermistor voltage detected by the voltage detector 44 (refer to "TEMPERATURE DETECTION VOLTAGE" in FIG. 5) is inputted to an input terminal of the subtractor 45. To the other input terminal of the subtractor 45, a target temperature voltage generated by the target temperature generator 43 is inputted. The target temperature generator 43 is provided, for example, with a central processing unit (CPU) and a D/A converter or the like (not illustrated) built in the CPU.

The subtractor 45 is configured to generate a temperature error by subtracting the temperature detection voltage from the target temperature voltage. The phase compensator 46 is configured to perform a phaser compensation (e.g., proportional, integral, and differential (PID)) control, which is suitable for a negative feedback control of temperature, on the temperature error generated by the subtractor 45, and is configured to output a drive command to the drive circuit 47. The drive circuit 47 is configured to generate a Peltier current in accordance with the drive command.

The thermistor 42, the voltage detector 44, the subtractor 45, the phaser compensator 46, the drive circuit 47, and the Peltier element 41 form a LD temperature control loop.

When an external environmental temperature is high, the Peltier element 41 transfers the heat generated in the semiconductor laser 11 to the heat radiation plate via the heat exchanger plate, with a heat flow corresponding to the Peltier current. The heat radiation plate releases the heat to the external environment. In this case, the Peltier element 41 cools the semiconductor laser 11. On the other hand, when the external environmental temperature is low, a reverse Peltier current is applied to the Peltier element 41, the polarity of the heat flow is reversed, and the semiconductor laser 11 is heated via the heat exchanger plate. In this case, the Peltier element 41 heats the semiconductor laser 11. By virtue of such an operation, the detected voltage of the thermistor 42 is maintained at a target voltage (or a target temperature) by the effect of the negative feedback of the temperature control loop, even when the external environmental temperature varies.

(Problems of Temperature Control)

In a Fabry-Perot semiconductor laser, even if the drive current is constant, an emitted light power and an oscillation wavelength vary due to a temperature change of the element. Specifically, a threshold current of the laser oscillation exponentially increases with increasing temperature, and the emitted light power decreases. Moreover, due to a temperature dependency of a refractive index or the like, an effective length of a resonator of a longitudinal mode is changed by a slight increase in temperature, and the oscillation wavelength is increased. If the temperature further increases, a gain difference from an adjacent mode is reversed, which may cause a wavelength jump for an abrupt transition to the adjacent mode, or a so-called mode hop. Under a temperature condition in which the mode hop occurs, there is no gain difference from the adjacent mode, and a so-called mode competition occurs. Alternatively, it may be in a state of so-called multiple mode in which there are a plurality of oscillation wavelengths.

In an optical measurement apparatus using the Laser Doppler effect, as in the optical measurement apparatus 100, interference of light is important. To improve measurement precision, it is necessary to maintain the laser oscillation in a single mode in which the interference of light is high. The studies by the present inventors have revealed that in the estimation of a flow volume of the scattered fluid by the laser flowmetry, when an oscillation state of a laser is transferred from the single mode to the multiple mode, the amplitude of the optical beat signal decreases due to a reduction in the interference of light, and accordingly, a measured S/N ratio decreases. To deal with such a problem, the negative feedback control of the temperature for maintaining a constant temperature of the semiconductor laser 11 is performed by the action of the LD temperature controller 40 illustrated in FIG. 5.

However, if the external environmental temperature changes, the temperature of the semiconductor laser 11, which is a target of the temperature control, is not necessarily kept constant, even if the detected temperature of the thermistor 42 is kept constant by the effect of the negative feedback control of the temperature.

Figure 6:
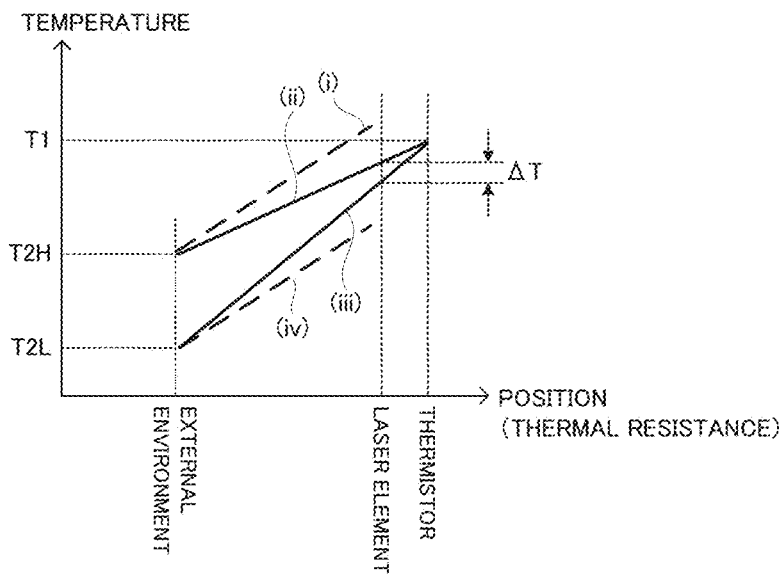
FIG. 6 is a diagram illustrating an example of a relation between the position of members and temperature in the LD temperature controller according to the first practical example.
Figure 7:
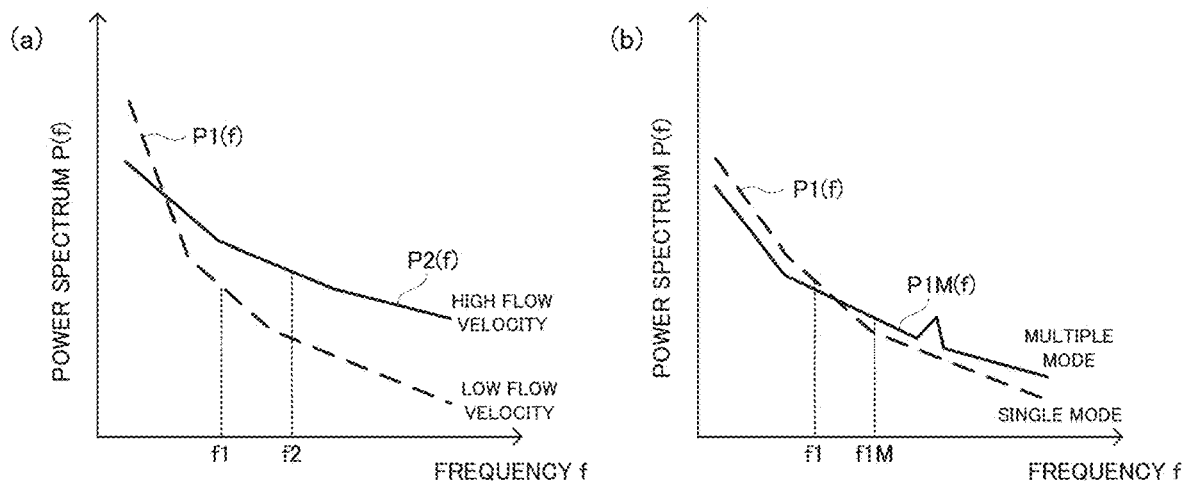
FIG. 7(a) and FIG. 7(b) are diagrams illustrating an example of a power spectrum.

The reason will be explained with reference to FIG. 5 and FIG. 6. FIG. 6 is a diagram illustrating an example of a relation between the position of members and temperature in the LD temperature controller according to the first practical example.

Regarding the heat flow between the thermistor 42 and the external environment, as illustrated in FIG. 5, there are heat conduction by the heat exchanger plate, heat conduction by the Peltier element 41, and heat conduction from the heat radiation plate to the external environment, and each member has thermal resistance. In addition, there is also thermal contact resistance on a contact surface between the members. Particularly in the case of natural cooling, the thermal resistance is relatively high in the heat conduction from the heat radiation plate to the external environment.

Moreover, in a process of heat conduction between the thermistor 42 and the semiconductor laser 11, as illustrated in FIG. 5, there are contact thermal resistance between the thermistor 42 and the heat exchanger plate, thermal resistance between a package of the semiconductor laser 11 and the element, and the like.

In FIG. 6, when the external environmental temperature is "T2H", which is relatively high, and when the semiconductor laser 11 is driven (i.e., when the semiconductor laser 11 is heated), if the Peltier current is zero (i.e., wherein there is no forcible heat transfer by the Peltier element 41), then, the temperature between the external environment and the semiconductor laser 11 is represented by a dashed line (i).

At this time, if a target temperature associated with the LD temperature controller 40 is set to "T1", if the semiconductor laser 11 is cooled by the Peltier element 41, and if the detected temperature of the thermistor 42 becomes "T1", then, the temperature between the external environment and the thermistor 42 is represented by a solid line (ii). Here, as described above, there is the thermal resistance between the thermistor 42 and the semiconductor laser 11, and thus, the temperature of the thermistor 42 does not match the temperature of the semiconductor laser 11.

In the same manner, when the external environmental temperature is "T2L", which is relatively low, and when the semiconductor laser 11 is driven, if the Peltier current is zero, the temperature between the external environment and the semiconductor laser 11 is represented by a dashed line (iv).

At this time, if the target temperature associated with the LD temperature controller 40 is set to "T1", if the semiconductor laser 11 is heated by the Peltier element 41, and if the detected temperature of the thermistor 42 becomes "T1", then, the temperature between the external environment and the thermistor 42 is represented by a solid line (iii). Even in this case, the temperature of the thermistor 42 does not match the temperature of the semiconductor laser 11.

Here, in particular, although the detected temperature of the thermistor 42 is "T1" in the both cases in which the semiconductor laser 11 is cooled by the Peltier element 41 and in which the semiconductor laser 11 is heated by the Peltier element 41, an error of ΔT (i.e., a difference between the solid line (ii) and the solid line (iii) in the position of the semiconductor laser 11) is caused in the temperature of the semiconductor laser 11. The error ΔT will not be zero unless the thermal resistance between the thermistor 42 and the semiconductor laser 11 is zero. In other words, in reality, it is hardly possible to set the error ΔT to zero.

Even if the target temperature (i.e., the detected temperature of the thermistor 42) can be maintained at a predetermined value (which is "T1" herein) by the effect of the negative feedback of the temperature control loop associated with the LD temperature controller 40, if the external environmental temperature changes, relatively significantly, then, the temperature of the semiconductor laser 11 slightly changes.

In the Fabry-Perot semiconductor laser, the temperature for a transition between the modes ranges within several degrees C., and in order to maintain the single mode, it is necessary to control a temperature change of the semiconductor laser 11 to be less than or equal to one degree C. Thus, if the change in the external environmental temperature is relatively large, the temperature control of the semiconductor laser 11 is hardly appropriately performed only by the temperature control loop associated with the LD temperature controller 40.

(Average Frequency)

Next, the average frequency fm will be explained with reference to FIG. 7(a) and FIG. 7(b). FIG. 7(a) and FIG. 7(b) are diagrams illustrating an example of a power spectrum.

As illustrated in FIG. 7(a), a power spectrum P1(f) when the blood that flows inside the target to be measured has a relatively low flow velocity is concentrated to relatively low frequencies. Thus, when the flow velocity is relatively low, the average frequency is "f1", which is relatively low. On the other hand, a power spectrum P2(f) when the blood that flows inside the target to be measured has a relatively high flow velocity is concentrated to relatively high frequencies. Thus, when the flow velocity is relatively high, the average frequency is "f2", which is relatively high.

FIG. 7(b) illustrates an example of the power spectrum when the blood that flows inside the target to be measured has a constant flow velocity, but the oscillation mode of the semiconductor laser 11 varies. The average frequency of the power spectrum P1(f) is "f1" when the semiconductor laser 11 oscillates in the single mode.

On the other hand, a power spectrum P1M(f) when the semiconductor laser 11 oscillates in the multiple mode has less low frequency components and more high frequency components than those of the power spectrum P1(f). This is because the amplitude of the optical beat signal decreases due to a reduction in the interference of light in the multiple mode. In particular, it is considered that the increase in the high frequency component is associated with impulse noise caused by the mode hop. As a result, the average frequency of the power spectrum P1M(f) is "f1M".

As illustrated in FIG. 7(a), the average frequency increases with increasing flow velocity. Thus, when the semiconductor laser 11 oscillates in the multiple mode, even if the flow velocity is the same, a higher flow velocity is erroneously estimated, in comparison with when the semiconductor laser 11 oscillates in the single mode.

If the change in the external environmental temperature is relatively large, the temperature control of the semiconductor laser 11 is hardly appropriately performed only by the LD temperature controller 40, and the flow velocity is likely erroneously estimated due to the mode hop.

(Relation Between Temperature and Average Frequency)

Figure 8:
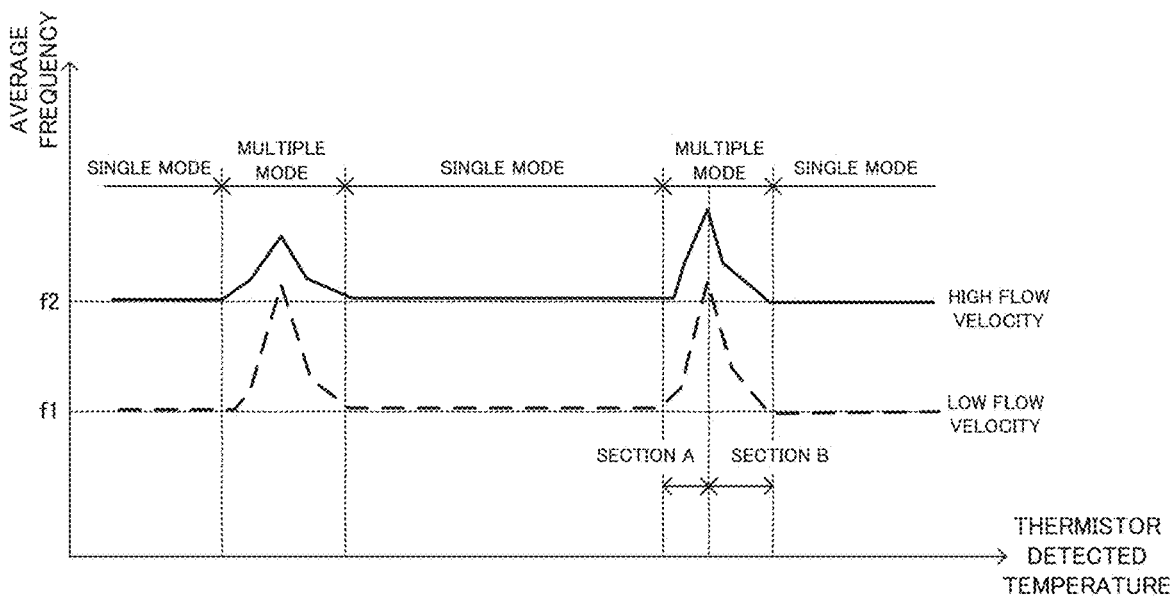
FIG. 8 is a diagram illustrating an example of a relation between a detected temperature of a thermistor and the average frequency.

FIG. 8 illustrates an example of a relation between the detected temperature of the thermistor 42 (≈the temperature of the semiconductor laser 11) and the average frequency. As illustrated in FIG. 8, when the detected temperature of the thermistor 42 changes, the oscillation mode of the semiconductor laser 11 also changes between the single mode and the multiple mode, alternately and repeatedly. When the oscillation mode of the semiconductor laser 11 is the single mode, the flow velocity does not change and the average frequency also does not change (specifically, when the flow velocity is relatively low, the average frequency is "f1", and when the flow velocity is relatively high, the average frequency is "f2"). On the other hand, When the oscillation mode of the semiconductor laser 11 is the multiple mode, even if the flow velocity does not change, the average frequency changes, irregularly.

The temperature of the semiconductor laser 11 also changes due to the heat generated in the semiconductor laser 11, in addition to the temperature control loop associated with the LD temperature controller 40. Here, an amount or quantity of the heat of the semiconductor laser 11 varies depending on the magnitude or the drive current supplied to the semiconductor laser 11.

When the oscillation mode of the semiconductor laser 11 is the multiple mode in a section A in FIG. 8, if the heat generation of the semiconductor laser 11 is prevented by reducing the drive current supplied to the semiconductor laser 11, the temperature of the semiconductor laser 11 is reduced, and the oscillation mode can be changed from the multiple mode to the single mode. In the same manner, when the oscillation mode of the semiconductor laser 11 is the multiple mode in a section B in FIG. 8, if the heat generated in the semiconductor laser 11 is increased by increasing the drive current supplied to the semiconductor laser 11, the temperature of the semiconductor laser 11 is increased, and the oscillation mode can be changed from the multiple mode to the single mode.

The present inventors, considering this point, have appropriately controlled the drive current supplied to the semiconductor laser 11, thereby transferring the oscillation mode from the multiple mode to the single mode, so that the erroneous detection of the flow velocity is prevented. Specifically, the optical measurement apparatus 100 is configured as follows.

(Drive Current Search Loop)

The optical measurement apparatus 100 is further provided with the disturbance generator 31, the synchronization detector 32, the phase compensator 33, the reference current unit 34, the subtractor 35, and the adder 36 (refer to FIG. 1).

Figure 10:
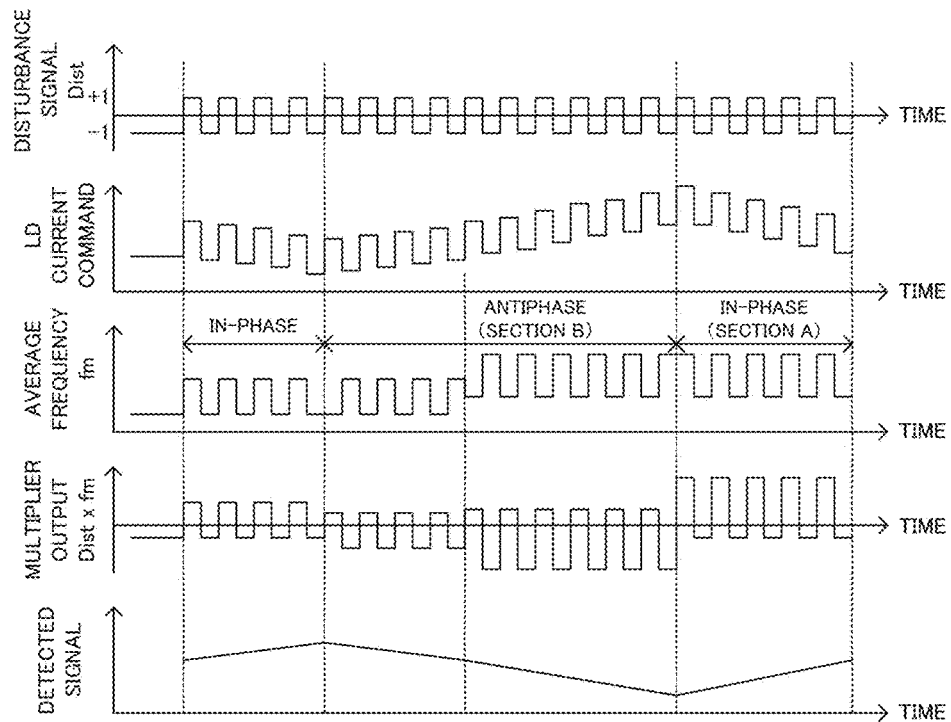
FIG. 10 is a diagram illustrating an example of each of a disturbance signal, an LD current command, the average frequency, a multiplier output, and a detected signal.

The disturbance generator 31 is configured to generate a disturbance signal. The disturbance signal may be, for example, as illustrated in FIG. 10, a rectangular wave with an amplitude of ±1, a repetition period of T, and a pulse duty ratio of 50%. The repetition period T of the disturbance signal may be set to a time that is longer than twice the time in which the data of n points required for FFT on the frequency analyzer 25 can be obtained. The reason is that conditioning setting is performed on the optical measurement apparatus 100 such that the average frequency fm can be calculated from at least one or more FFT results in a half period of the disturbance signal.

Figure 9:
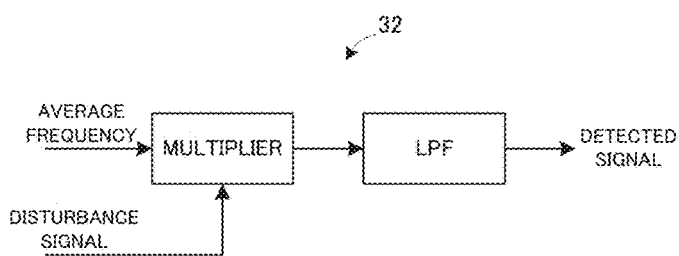
FIG. 9 is a conceptual diagram illustrating an example of a synchronization detector according to the first practical example.

A specific example of the synchronization detector 32 will be explained with reference to FIG. 9. FIG. 9 is a conceptual diagram illustrating an example of the synchronization detector 32 according to the first practical example.

In FIG. 9, the synchronization detector 32 is provided with a multiplier and a low-pass filter (LPF). The average frequency fm calculated by the average frequency calculator 26 is an input terminal of the multiplier. To the other input terminal of the multiplier, the disturbance signal generated by the disturbance generator 31 is inputted. The multiplier is configured to multiply the average frequency fm and the disturbance signal, thereby calculating a phaser difference between the two. In other words, the multiplier may operate as a phase comparator. An output of the multiplier is averaged by the LPF, and a detected signal is outputted (refer to FIG. 10).

The phase compensator 33 is configured to perform a predetermined phase compensation control on the detected signal outputted from the synchronization detector 32. An output from the phase compensator 33 is inputted to an input terminal of the subtractor 35. To the other input terminal of the subtractor 35, a reference current is inputted from the reference current unit 34. The subtractor 35 is configured to output a value obtained by subtracting the output of the phase compensator 33 on the basis of the reference current, as an error signal.

The error signal is inputted to an input terminal of the adder 36. To the other input terminal of the adder 36 the disturbance signal is inputted. The adder 36 is configured to generate an LD current command by adding the disturbance signal to the error signal. Due to the addition of the disturbance signal, the LD current command makes micro vibration (wobbling) in synchronization with the disturbance signal (refer to FIG. 10).

Next, the detected signal and the like in the sections A and B (i.e., in the multiple mode) in FIG. 8 will be explained with reference to FIG. 10. FIG. 10 is a diagram illustrating an example of each of the disturbance signal, the LD current command, the average frequency, the multiplier output, and the detected signal.

In the section A in FIG. 8, as the detected temperature of the thermistor 42 (in other words, the drive current of the semiconductor laser 11) becomes higher, the average frequency also becomes higher. In other words, in the section A, a slope (i.e., a derivative) of the average frequency is "positive". On the other hand, in the section B, as the detected temperature of the thermistor 42 becomes higher, the average frequency becomes lower. In other words, in the section B, the slope of the average frequency is "negative".

Here, the LD current command, as described above, makes micro vibration in synchronization with the disturbance signal. Thus, the drive current supplied to the semiconductor laser 11 also makes micro vibration in synchronization with the disturbance signal. As a result, the average frequency fm calculated by the average frequency calculator 26 also makes micro vibration in synchronization with the disturbance signal.

In the section A in FIG. 8, since the slope of the average frequency is "positive", the micro vibration of the average frequency fm calculated by the average frequency calculator 26 is in phase with the disturbance signal (refer to "IN PHASE (SECTION A) of the average frequency fm in FIG. 10). Therefore, the output of the multiplier of the synchronization detector 32 is positive. Thus, by the effect of integration of the LPF of the synchronization detector 32, the detected signal increases.

On the other hand, in the section B, since the slope of the average frequency is "negative", the micro vibration of the average frequency fm calculated by the average frequency calculator 26 is in antiphase with the disturbance signal (refer to "ANTIPHASE (SECTION B) of the average frequency fm in FIG. 10). Therefore, the output of the multiplier of the synchronization detector 32 is negative. Thus, the detected signal decreases.

As described above, on the subtractor 35, the output of the phase compensator 33 is subtracted from the reference current, and the error signal is outputted. In the section A, since the detected signal increases, the output of the phase compensator 33, which reflects the detected signal, also increases. As a result, the error signal decreases. Then, the LD current command also decreases, and the drive current supplied to the semiconductor laser 11 also decreases. If the temperature of the semiconductor laser 11 decreases due to the reduction in the drive current, the oscillation mode of the semiconductor laser 11 is transferred from the multiple mode (section A) to the single mode (a section adjacent to the section A on the left side in FIG. 8).

In the same manner, in the section B, since the detected signal decreases, the output of the phase compensator 33 also decreases. As a result, the error signal increases. Then, the LD current command also increases, and the drive current supplied to the semiconductor laser 11 also increases. If the temperature of the semiconductor laser 11 increases due to the increase in the drive current, the oscillation mode of the semiconductor laser 11 is transferred from the multiple mode (section B) to the single mode (a section adjacent to the section B on the right side in FIG. 8).

As described above, on the optical measurement apparatus 100, the disturbance generator 31, the synchronization detector 32, the phase compensator 33, the subtractor 35, the adder 36, and the average frequency calculator 26 and the like form a drive current search loop. By this drive current search loop, the drive current supplied to the semiconductor laser 11 is appropriately set.

Here, a specific example of each of the drive current and the average frequency in operation of the optical measurement apparatus 100 will be explained with reference to FIG. 11(a) and FIG. 11(b).

Suppose that, at a time point t0 in FIG. 11(a), the drive current supplied to the semiconductor laser 11 is "i2−Δi" and the average frequency is "f2+Δf". In this case, as illustrated in FIG. 11(b), the oscillation mode of the semiconductor laser 11 is the multiple mode.

At a time point t1 in FIG. 11(a), if the drive current search loop is turned on by a CPU (not illustrated) for integrally controlling the optical measurement apparatus 100, the drive current makes micro vibration in synchronization with the disturbance signal (which is illustrated in a thick line due to scale in FIG. 11(a)).

As illustrated in FIG. 11(a), by the effect of the negative feedback of the drive current search loop, the drive current gradually increases from the time point t1, and eventually converges on "i2" (wherein it is considered to be in a steady state at a time point t2). At this time, the average frequency gradually decreases from the time point t1, and eventually converges on "f2".

As illustrated in FIG. 11(b), when the drive current is "i2", the oscillation mode of the semiconductor laser 11 is the single mode. Thus, it can be said that the average frequency "f2" is an appropriate value.

(Relation Between Drive Current Search Loop and Temperature Control Loop)

There is no choice but to design the frequency of the temperature control loop by the LD temperature controller 40 (refer to FIG. 5) in a band that is equal to or less than 1 Hz. It is because the temperature detected by the thermistor 42 does not instantaneously change (i.e., time responsiveness is low) due to a heat capacity of the members that constitute the temperature control loop.

On the other hand, the frequency of the disturbance signal in the drive current search loop can be set, for example, to be in a band that is equal to or greater than 50 Hz. It is because it is relatively easy to locally change the temperature of the semiconductor laser 11 (i.e., time responsiveness is high) due to a change in the drive current.

It is thus considered that the local change in the temperature of the semiconductor laser 11 by the drive current search loop does not influence the temperature control loop. In other words, it is considered that the drive current search loop does not interfere with the temperature control loop.

(Effect)

According to the optical measurement apparatus 100, even if the oscillation mode of the semiconductor laser 11 is the multiple mode, which is not appropriate for the measurement of the flow velocity of the blood that flows inside the target to be measured, the oscillation mode can be transferred to the single mode, which is preferable for the measurement of the flow velocity, by the drive current search loop described above. Thus, according to the optical measurement apparatus 100, it is possible to prevent a change in the properties of the laser light emitted from the semiconductor laser 11, and it is possible to appropriately measure the flow velocity.

Note that the drive current search loop according to the first practical example is intended to maintain the oscillation mode of the semiconductor laser 11 in the single mode, and that it is not intended to maintain the wavelength of the laser light emitted from the semiconductor laser 11 at a predetermined value.

There is a possibility that the wavelength of the laser light emitted from the semiconductor laser 11 changes due to a change in the drive current supplied to the semiconductor laser 11; however, for example, as illustrated in FIG. 11(b), as long as the single mode is maintained, it is possible to obtain the average frequency that is appropriate, and it is therefore possible to appropriately measure the flow velocity.

First Modified Example

As adjustment before shipping products or before the measurement by the optical measurement apparatus 100, the specified scattered fluid that flows at a specified velocity may be measured by the optical measurement apparatus 100 while the temperature of the semiconductor 11 is changed by the LD temperature controller 40, and the relation between the detected temperature of the thermistor 42 and the average frequency may be obtained, for example, as illustrated in FIG. 8. Then, the optical measurement apparatus 100 may be configured to set an initial value of the target temperature associated with the LD temperature controller 40 such that the oscillation mode of the semiconductor 11 is the single mode, on the basis of the obtained relation.

By virtue of such a configuration, for example, even if the external environmental temperature is shifted from the temperature in designing the optical measurement apparatus 100 (e.g., a normal temperature), or even if laser oscillation characteristics to temperature change due to an aged deterioration or secular change of the semiconductor laser 11 or the like, it is possible to appropriately set the initial value of the target temperature associated with the LD temperature controller 40.

In addition, if the initial value of the target temperature associated with the LD temperature controller 40 is appropriately set, it is possible to prevent that the drive current becomes excessively high or excessively low, in the drive current search loop. As a result, it is possible to prevent that an element life of the semiconductor laser 11 is reduced due to the excessively high drive current, and that a SN ratio is reduced due to the excessively low drive current and the error of a measurement result increases.

Second Modified Example

Figure 12:
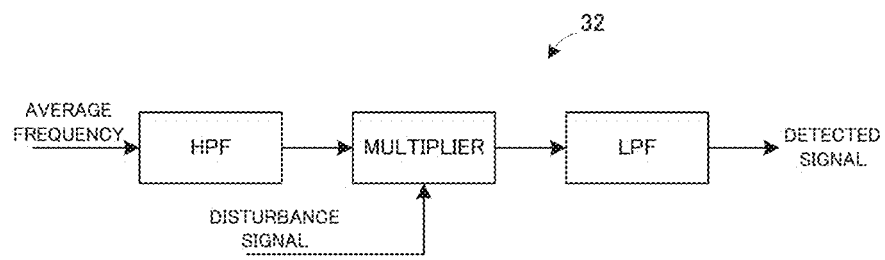
FIG. 12 is a conceptual diagram illustrating an example of a synchronization detector according to a second modified example of the first practical example.

A specific configuration of the synchronization detector 32 is not limited to the configuration illustrated in FIG. 9, but may also be, for example, a configuration illustrated in FIG. 12.

The blood that flows in the tubing that constitutes the blood circuit of the artificial dialysis apparatus, which is a measurement target, is transferred by a tubing pump (e.g., a pump of a type of drawing the tubing with a roller and pressing out the blood in the tubing) or the like. Thus, the flow velocity has a pulsation component corresponding to the number of revolutions of the roller of the tubing pump. In order that the frequency of the pulsation component is lower than the frequency of the disturbance signal, the frequency of the disturbance signal is set in advance.

Figure 13:
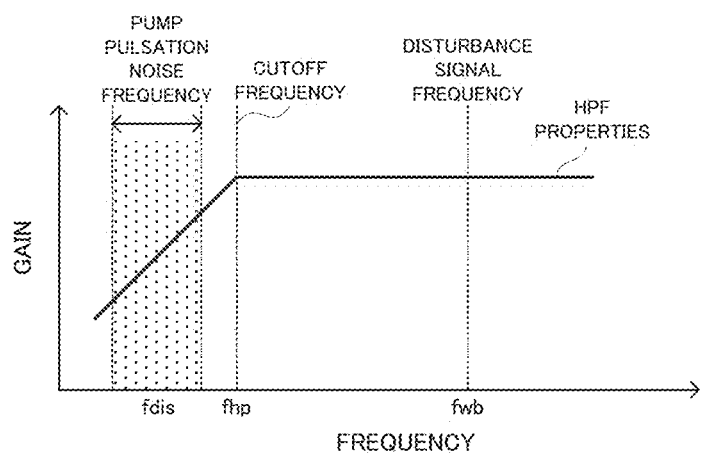
FIG. 13 is a characteristic diagram illustrating an example of filter properties of a HPF, which is included in the synchronization detector according to the second modified example of the first practical example.

As illustrated in FIG. 12, by providing a high-pass filter (HPF) having, for example, frequency characteristics illustrated in FIG. 13 before the multiplier of the synchronization detector 32, it is possible to reduce a noise component caused by the pulsation component. As a result, a SN ratio of the detected signal can be improved.

As illustrated in FIG. 13, by setting a frequency fwb of the disturbance signal to be higher than a cutoff frequency fhp of the HPF, it is possible to relatively efficiently detect the signal component that changes in synchronization with the disturbance signal, on the synchronization detector 32.

Second Practical Example

An optical measurement apparatus according to a second practical example of the present invention will be explained with reference to FIG. 14. The second practical example is the same as the first practical example described above, except that the configuration is partially different. Thus, in the second practical example, the same explanation as that in the first practical example will be omitted, and the same reference numerals will carry in the same parts in the drawings. An explanation will be given only to basically different points with reference to FIG. 14.

(Configuration of Optical Measurement Apparatus)

Figure 14:
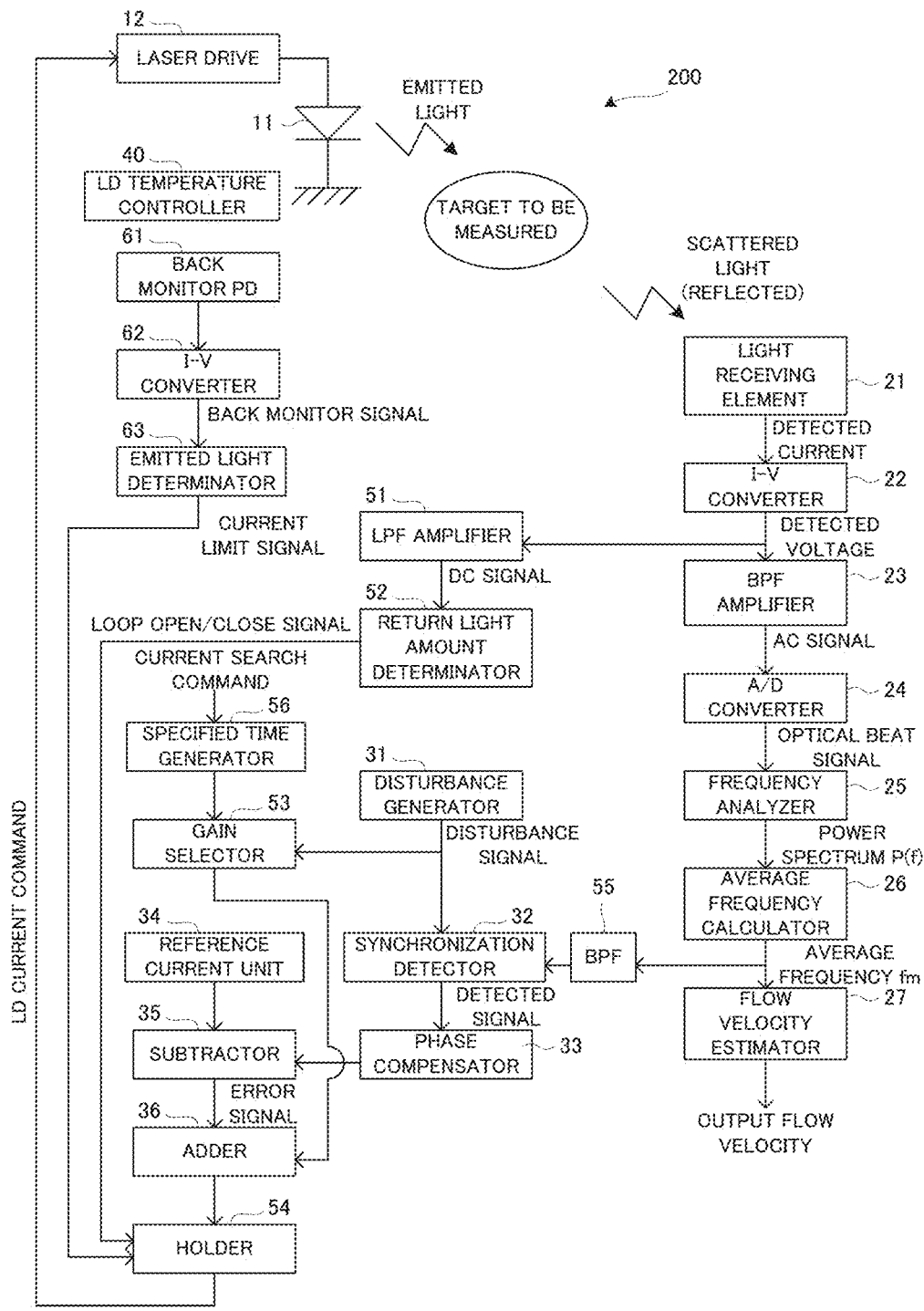
FIG. 14 is a block diagram illustrating a configuration of an optical measurement apparatus according to a second practical example.

In FIG. 14, an optical measurement apparatus 200 is provided with an LPF amplifier 51, a return light amount determinator 52, a gain selector 53, a holder 54, a BPF 55, a specified time generator 56, a back monitor photo detector (PD) 61, an I-V converter 62, and an emitted light determinator 63.

The average frequency fm outputted from the average frequency calculator 26 is inputted to the BPF 55. A cutoff frequency on a low frequency side of the BPF 55 may be, for example, the frequency hfp illustrated in FIG. 13. A cutoff frequency on a high frequency side of the BPF 55 is set to be higher than the frequency of the disturbance signal.

The LPF amplifier 51 is configured to cut a high frequency component, which is included in the voltage signal outputted from the I-V converter 22, and amplifies the rest. A DC signal outputted from the LPF amplifier 51 is inputted to the return light amount determinator 52.

Here, when the fluid that flows inside the target to be measured does not include or hardly includes scattered light, the level (or light amount) of return light, which returns to the light receiving element 21, decreases, wherein the light receiving element 21 is placed to mainly receive reflected light, which is backscattered light. As a result, the detected voltage outputted from the I-V converter 22 decreases, and the level of the DC signal outputted from the LPF amplifier 51 also decreases.

The return light amount determinator 52 is configured to determine that the fluid does not include or hardly includes a scatterer and is configured to output a loop open/close signal that allows the drive current search loop in an open state, when the level of the DC signal is relatively low. On the other hand, the return light amount determinator 52 is configured to determine that the fluid includes a scatterer and is configured to output a loop open/close signal that allows the drive current search loop in a closed state when the level of the DC signal is relatively high.

The loop open/close signal is inputted to the holder 54. When the loop open/close signal that allows the closed state is inputted to the holder 54, the LD current command, which changes in accordance with a change in the detected signal, is outputted from the holder 54, as in the first practical example described above. On the other hand, when the loop open/close signal that allows the open state is inputted to the holder 54, the LD current command immediately before the transition from the closed state to the open state is maintained in a period in which the loop open/close signal that allows the open state is inputted.

The back monitor PD 61 is configured to detect a light amount of the light emitted from the semiconductor laser 11 and to output a detected current corresponding to the light amount. The I-V converter 62 is configured to convert the detected current outputted from the back monitor PD 61 to a voltage signal (refer to "BACK MONITOR SIGNAL" in FIG. 14). A back monitor signal outputted from the I-V converter 62 is inputted to the emitted light determinator 63.

The emitted light determinator 63 is configured to output a current limit signal indicating a limit state, when the level of the back monitor signal is relatively high (i.e., when the power of the light emitted from the semiconductor laser 11 is relatively high), or when the level of the back monitor signal is significantly low (i.e., when the power of the light drops due to the excessively low drive current, the SN ratio decreases, and the error of the measurement result increases). On the other hand, the emitted light determinator 63 is configured to output a current limit signal indicating a normal state, when the level of the back monitor signal is not as described above and is preferable for the measurement of the flow velocity (i.e., when the power of the light emitted from the semiconductor laser 11 is preferable for the measurement of the flow velocity).

The current limit signal is inputted to the holder 54. When the current limit signal that indicates the normal state is inputted to the holder 54, the LD current command, which changes in accordance with a change in the detected signal, is outputted from the holder 54, as in the first practical example described above. On the other hand, when the current limit signal that indicates the limit state is inputted to the holder 54, the LD current command immediately before the transition from the normal state to the limit state is maintained in a period in which the current limit signal that indicates the limit state is inputted.

The specified time generator 56 is configured to transmit a signal indicating a specified time, to the gain selector 53, when receiving a current search command from a CPU (not illustrated) for integrally controlling the optical measurement apparatus 200. The gain selector 53 that has received the signal indicating the specified time is configured to select a gain that is higher, by the specified time, than those in the normal case.

(Technical Effect)

1. When Fluid does not Include Scatterer

When the fluid that flows inside the target to be measured does not include or hardly includes a scatterer, the optical beat signal cannot be obtained, and thus, the average frequency fm corresponding to a flow volume of the fluid cannot be obtained. At this time, if the drive current search loop is turned on, the average frequency fm changes, regardless of whether the oscillation mode of the semiconductor laser 11 is the single mode or the multiple mode. This may likely result in a phenomenon in which the LD current command unilaterally increases or decreases. In other words, it may likely cause a phenomenon in which the drive current unilaterally increases or decreases.

In the second practical example, when the level of the DC signal outputted from the LPF amplifier 51 is relatively low, the return light amount determinator 52 may output the loop open/close signal that allows the drive current search loop in the open state. As a result, the LD current command immediately before the transition from the closed state to the open state is maintained in the period in which the loop open/close signal that allows the open state is inputted to the holder 54.

In addition, when the level of the back monitor signal outputted from the I-V converter 62 is relatively high, or when the level of the back monitor signal is significantly low, the emitted light determinator 63 may output the current limit signal indicating the limit state. The LD current command immediately before the transition from the normal state to the limit state is maintained in the period in which the current limit signal that indicates the limit state is inputted.

By virtue of such a configuration, it is possible to prevent the phenomenon in which the LD current command and the drive current unilaterally increase or decrease. It is thus possible to stably operate the drive current search loop. In addition, it is possible to prevent the deterioration of the semiconductor laser 11.

2. Reduction of Time Required for Drive Current Search

Figure 11:
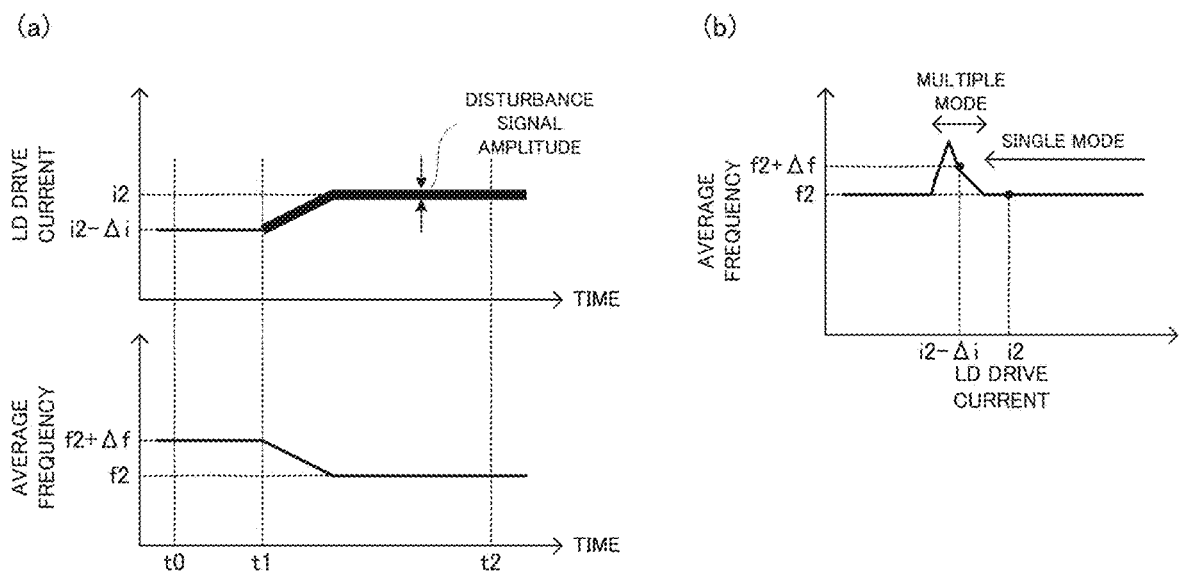
FIG. 11(a) and FIG. 11(b) are diagrams illustrating an example of each of a drive current and the average frequency in driving the optical measurement apparatus according to the first practical example.

For example, if the drive current "i2−Δi" at the time point t0 in FIG. 11(*a*) is relatively significantly separated from the drive current "i2" in the steady state, a time required to reach the steady state is relatively long.

When the gain that is higher, by the specified time, than those in the normal case is selected by the gain selector 53, the amplitude of the disturbance signal is relatively large. Ten, a variation component of the average frequency fm inputted to the synchronization detector 32 is also relatively large. As a result, the amplitude of the detected signal also increases. This action increases a loop gain of the drive current search loop. Thus, transient characteristics are improved (specifically, a settling time is reduced), and the time required to reach the steady state is reduced.

Therefore, it is possible to set a period in which the oscillation mode of the semiconductor laser 11 is the multiple mode to be relatively short, and it is also possible to transfer the oscillation mode from the multiple mode to the single mode in a relatively short time.

In addition, it is possible to reduce a possibility of promoting a fluctuation state of the drive current by limiting a high gain state for the specified time. As a result, it is possible to stably operate the drive current search loop.

Modified Example

In addition to the light receiving element 21, there may be provided a light receiving element for generating a DC signal inputted to the return light amount determinator 52. This light receiving element desirably has a relatively large detection area. By virtue of such a configuration, the detected current outputted from the light receiving element increases, and a SN ratio of the DC signal can be improved.

In addition, if an electrostatic capacity of the light receiving element 21 is set to be relatively small and the detection area is set to be relatively small, it is then possible to increase a detectable flow velocity upper limit of the optical measurement apparatus 100.

The present invention is not limited to the aforementioned embodiments and examples, but various changes may be made, if desired, without departing from the essence or spirit of the invention which can be read from the claims and the entire specification. An optical measurement apparatus, an optical measurement method, a computer program, and a recording medium that involve such changes are also intended to be within the technical scope of the present invention.

Description of Reference Numerals and Letters 11 semiconductor laser
12 laser drive unit
21 light receiving element
22, 62 I-V converter
23 BPF amplifier
24 A/D converter
25 frequency analyzer
26 average frequency calculator
27 flow velocity estimator
31 disturbance generator
32 synchronization detector
33, 46 phase compensator
34 reference current unit
35, 45 subtractor
36 adder
40 LD temperature controller
41 Peltier element
42 thermistor
43 target temperature generator
44 voltage detector
47 drive circuit
51 LPF amplifier
52 return light amount determinator
53 gain selector
54 holder
55 BPF
61 back monitor PD
63 emitted light determinator

The invention claimed is:

1. An optical measurement apparatus comprising:
a light source configured to irradiate, with light, a fluid flowing within a measurement target, a temperature of the light source being changed by changing a drive current of the light source;
a light receiver configured to receive scattered light of irradiated light from the measurement target and from the fluid flowing within the measurement target, and configured to output a light receiving signal corresponding to intensity of the scattered light scattered by the fluid and by the measurement target, the light receiving signal including an optical beat signal;
a frequency analyzer configured to use the optical beat signal of the light receiving signal to calculate a power spectrum of the light receiving signal and configured to output a frequency analysis signal;
a disturbance generator configured to generate a disturbance signal for fluctuating the drive current, which disturbance signal is supplied to said light source to change the temperature of the light source;
a synchronization detector configured to detect a phase difference between the frequency analysis signal and the disturbance signal; and
an adjuster configured to adjust the drive current by determining whether increasing or decreasing the drive current on the basis of the phase difference and the disturbance signal.

2. The optical measurement apparatus according to claim 1, wherein the beat signal is caused by a Doppler shift of the irradiation light caused by a moving velocity of the fluid flowing within the measurement target.

3. The optical measurement apparatus according to claim 2, wherein the frequency analysis signal is compared with the disturbance signal by the synchronization device after being passed through a filter for selectively passing a frequency component of a predetermined frequency band, which includes a frequency associated with the disturbance signal.

4. The optical measurement apparatus according to claim 1, wherein
the fluid is transferred by a pump, and
a frequency associated with the disturbance signal is higher than a pulsation frequency of the fluid, which is caused by the pump.

5. The optical measurement apparatus according to claim 1, wherein
said light source is a semiconductor laser, and
said adjuster is configured to adjust the drive current by determining whether increasing or decreasing the drive current on the basis of the phase difference such that the semiconductor laser oscillates in a single mode.

6. The optical measurement apparatus according to claim 1, comprising:
a temperature controller configured to control a temperature of said light source; and
a temperature setting device (i) configured to obtain a relation between the temperature of said light source and interference of the light emitted from said light source, while controlling said temperature controller to change the temperature of said light source, and (ii) configured to set a target temperature associated with said temperature controller on the basis of the obtained relation, before measurement of the measurement target.

7. The optical measurement apparatus according to claim 1, comprising:
a first determinator configured to determine whether or not the fluid includes a scatterer on the basis of the light receiving signal; and
a first light source controller configured to control a power of the light emitted from said light source, on the basis of a determination result of said first determinator.

8. The optical measurement apparatus according to claim 1, comprising:
a light amount monitor configured to detect a power of the light emitted from said light source;

a second determinator configured to determine whether or not the detected power is within a predetermined range; and a second light source controller configured to control the power of the light emitted from said light source, on the basis of a determination result of said second determinator.

9. The optical measurement apparatus according to claim 1, comprising: a gain selector configured to change an amplitude of the disturbance signal generated by said disturbance generator.

10. The optical measurement apparatus according to claim 1, wherein the disturbance generator is configured to generate the disturbance signal as a rectangular wave with a repetition period and a pulse duty ratio.

11. The optical measurement apparatus according to claim 1, wherein the disturbance generator is configured to generate the disturbance signal as a rectangular wave with an amplitude of ±1, a repetition period of T, and a pulse duty ratio of 50%.

12. The optical measurement apparatus of claim 1, further comprising an average frequency calculator configured to calculate an average frequency (fm) on the basis of the power spectrum P(f) calculated by the frequency analyzer, wherein the frequency analysis signal comprises the average frequency (fm) and the synchronization detector uses the average frequency (fm) in detecting the phase difference between the frequency analysis signal and the disturbance signal.

13. An optical measurement method in an optical measurement apparatus including: a light source configured to irradiate a measurement target in which fluid flows, with light; and a light receiver configured to receive scattered light of irradiated light from the measurement target and configured to output a light receiving signal corresponding to intensity of the scattered light, said optical measurement method comprising:

a process of generating a disturbance signal for fluctuating a drive current, which disturbance signal is supplied to the light source to change a temperature of the light source;

a process of frequency analysis using an optical beat signal of the light receiving signal to calculate a power spectrum of the light receiving signal and configured to output a frequency analysis signal;

a process of detecting a phase difference between a signal generated on the basis of the frequency analysis signal and the disturbance signal; and a process of adjusting the drive current by determining whether increasing or decreasing the drive current on the basis of the phase difference and the disturbance signal.

14. A non-transitory computer-readable tangible recording medium on which a computer program is recorded, wherein the computer program for making a computer, which is provided in an optical measurement apparatus including: a light source configured to irradiate a measurement target in which fluid flows, with light; and a light receiver configured to receive scattered light of irradiated light from the measurement target and configured to output a light receiving signal corresponding to intensity of the scattered light, function as:

a frequency analyzer configured to use an optical beat signal of the light receiving signal to calculate a power spectrum of the light receiving signal and configured to output a frequency analysis signal;

a disturbance generator configured to generate a disturbance signal for fluctuating a drive current, which is supplied to said light source to change a temperature of the light source;

a synchronization detector configured to detect a phase difference between the frequency analysis signal and the disturbance signal; and an adjuster configured to adjust the drive current by determining whether increasing or decreasing the drive current on the basis of the phase difference and the disturbance signal.

\* \* \* \* \*